(12) United States Patent
Garlow et al.

(10) Patent No.: US 11,678,849 B2
(45) Date of Patent: *Jun. 20, 2023

(54) FILTER SYSTEM AND METHOD FOR IMAGING A SUBJECT

(71) Applicant: Medtronic Navigation, Inc., Louisville, CO (US)

(72) Inventors: David A. Garlow, Lynnfield, MA (US); Kyo C. Jin, Durham, NH (US)

(73) Assignee: Medtronic Navigation, Inc., Louisville, CO (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/321,741

(22) Filed: May 17, 2021

(65) Prior Publication Data
US 2021/0267561 A1   Sep. 2, 2021

Related U.S. Application Data

(63) Continuation of application No. 17/004,495, filed on Aug. 27, 2020, now Pat. No. 11,006,910, which is a continuation of application No. 16/386,636, filed on Apr. 17, 2019, now Pat. No. 10,758,194.

(51) Int. Cl.
*A61B 6/00*    (2006.01)
*G21K 1/10*    (2006.01)

(52) U.S. Cl.
CPC .............. *A61B 6/4035* (2013.01); *G21K 1/10* (2013.01)

(58) Field of Classification Search
CPC ......... A61B 6/4035; A61B 6/547; A61B 6/06; G21K 1/10
See application file for complete search history.

(56) References Cited

U.S. PATENT DOCUMENTS

| | | | |
|---|---|---|---|
| 4,528,685 A | 7/1985 | Kump et al. | |
| 5,555,283 A | 9/1996 | Shiu et al. | |
| 7,254,216 B2 | 8/2007 | Fhandiackal et al. | |
| 8,238,522 B2 | 8/2012 | Frey et al. | |
| 8,562,211 B2 | 10/2013 | Helm et al. | |
| 8,737,567 B2 | 5/2014 | Shah | |
| 8,891,847 B2 | 11/2014 | Helm et al. | |
| 8,971,495 B2 | 3/2015 | Shah | |
| 9,121,809 B2 | 9/2015 | Cox et al. | |
| 9,220,573 B2 | 12/2015 | Kendrick et al. | |
| 9,689,811 B2 | 6/2017 | Cox et al. | |
| 10,191,615 B2 | 1/2019 | Helm et al. | |

(Continued)

FOREIGN PATENT DOCUMENTS

KR    20160036128 A    4/2016

OTHER PUBLICATIONS www.renishaw.com/en/magnetic-encoder-modules-offer-non-contact-alternative-to-potentiometers, 4 pgs., printed Apr. 11, 2017.

(Continued)

*Primary Examiner* — David A Vanore
(74) *Attorney, Agent, or Firm* — Harness, Dickey & Pierce, P.L.C.

(57) ABSTRACT

A method and system is disclosed for acquiring image data of a subject. The image data can be collected with an imaging system using various selection techniques. The selection techniques may be used to assist in generating selected images for viewing. Selection techniques may include moving a filter to filter a selected portion of an imaging beam.

20 Claims, 8 Drawing Sheets

(56) References Cited

U.S. PATENT DOCUMENTS

| | | | |
|---|---|---|---|
| 10,517,680 B2 | 12/2019 | Moctezuma et al. | |
| 10,555,779 B2 | 2/2020 | Kemp et al. | |
| 10,682,103 B2 * | 6/2020 | Garlow | A61B 6/56 |
| 10,758,194 B1 * | 9/2020 | Garlow | A61B 6/4035 |
| 10,806,413 B2 * | 10/2020 | Garlow | A61B 34/20 |
| 10,849,576 B2 * | 12/2020 | Garlow | A61B 6/032 |
| 11,006,910 B2 * | 5/2021 | Garlow | A61B 6/547 |
| 11,369,324 B2 * | 6/2022 | Garlow | A61B 6/4035 |
| 2007/0025520 A1 | 2/2007 | Thandiackal et al. | |
| 2011/0268325 A1 | 11/2011 | Teichman et al. | |
| 2017/0325776 A1 | 11/2017 | Cox et al. | |
| 2018/0035969 A1 | 2/2018 | Jin | |
| 2018/0310899 A1 | 11/2018 | Garlow et al. | |
| 2018/0310900 A1 | 11/2018 | Garlow et al. | |
| 2018/0310901 A1 | 11/2018 | Garlow et al. | |
| 2018/0345178 A1 | 12/2018 | Morris et al. | |
| 2022/0296185 A1 * | 9/2022 | Garlow | A61B 6/12 |

OTHER PUBLICATIONS

International Search Report and Written Opinion dated Jun. 26, 2020 in corresponding/related International Application No. PCT/US2020/028416.

* cited by examiner

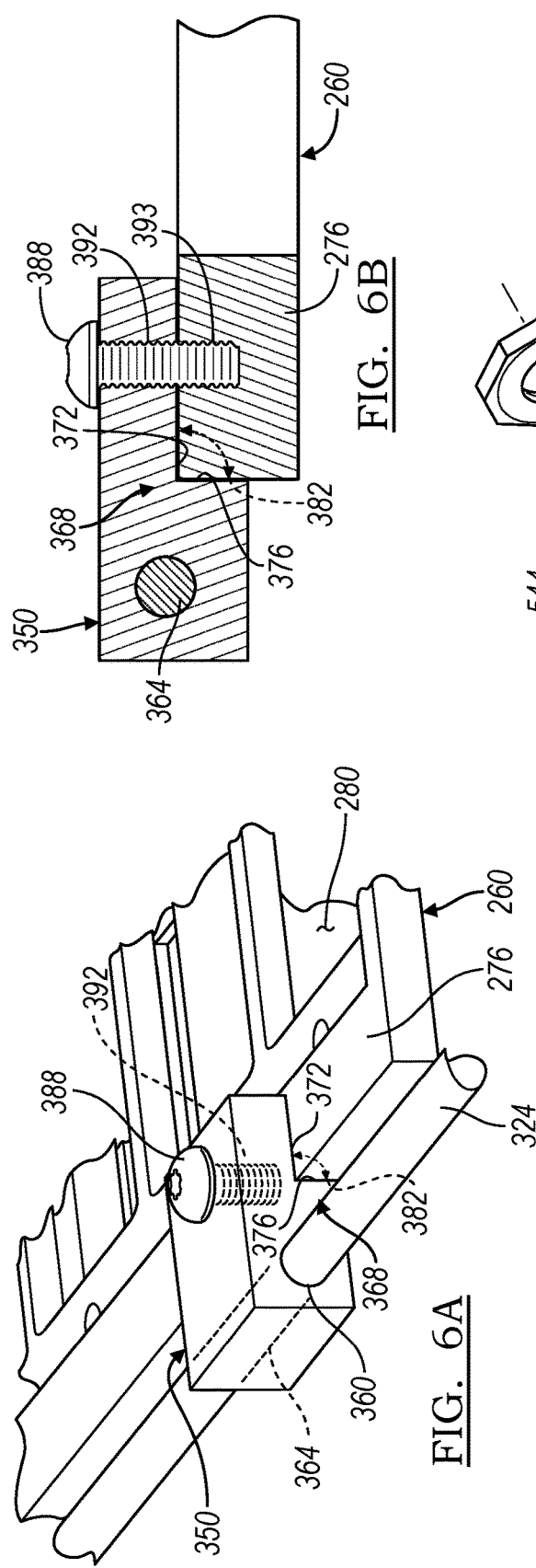
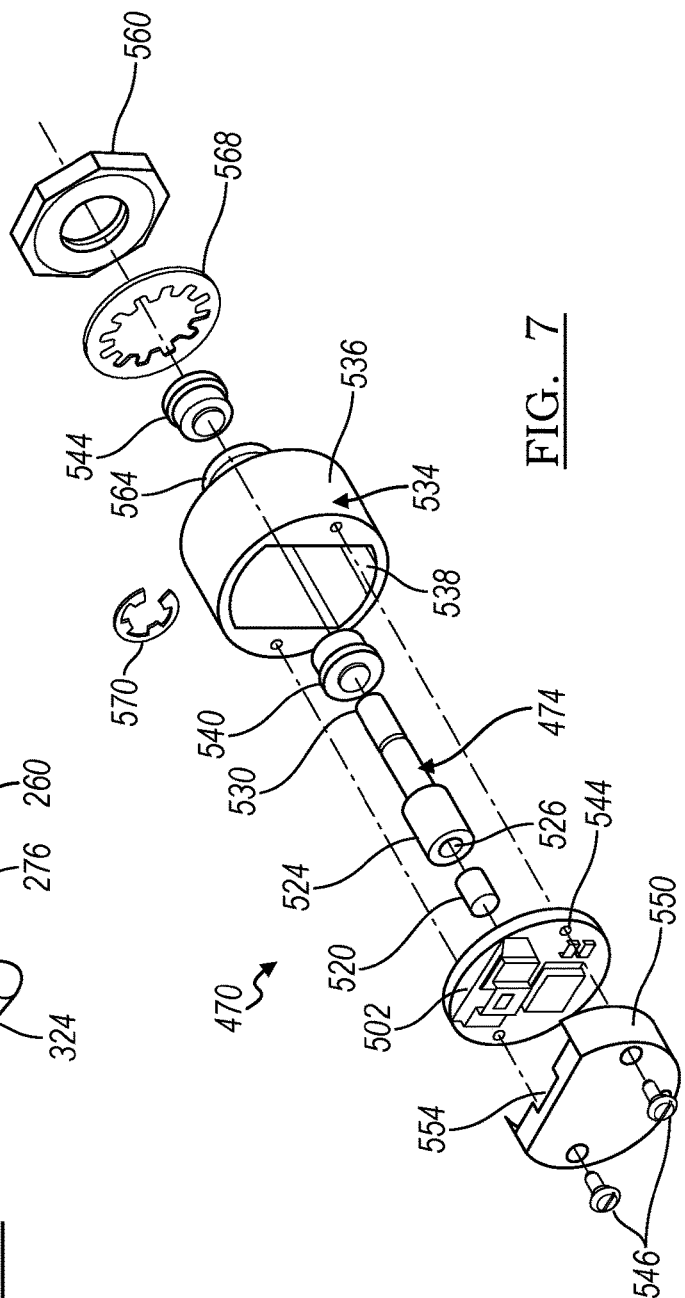

FILTER SYSTEM AND METHOD FOR IMAGING A SUBJECT

CROSS-REFERENCE TO RELATED APPLICATIONS

This application is a continuation of U.S. patent application Ser. No. 17/004,495 filed on Aug. 27, 2020, which is a continuation of U.S. patent application Ser. No. 16/386,636 filed on Apr. 17, 2019, now U.S. Pat. No. 10,758,194 issued on Sep. 1, 2020. The entire disclosures of the above applications are incorporated herein by reference.

FIELD

The present disclosure relates to imaging a subject, and particularly to a system to acquire image data with an adjustable collimator.

BACKGROUND

This section provides background information related to the present disclosure which is not necessarily prior art.

A subject, such as a human patient, may select or be required to undergo a surgical procedure to correct or augment an anatomy of the subject. The augmentation of the anatomy can include various procedures, such as movement or augmentation of bone, insertion of an implant (i.e. an implantable device), or other appropriate procedures. A surgeon can perform the procedure on the subject with images of the subject that can be acquired using imaging systems such as a magnetic resonance imaging (MRI) system, computed tomography (CT) system, fluoroscopy (e.g. C-Arm imaging systems), or other appropriate imaging systems.

Images of a subject can assist a surgeon in performing a procedure including planning the procedure and performing the procedure. A surgeon may select a two dimensional image or a three dimensional image representation of the subject. The images can assist the surgeon in performing a procedure with a less invasive technique by allowing the surgeon to view the anatomy of the subject without removing the overlying tissue (including dermal and muscular tissue) when performing a procedure.

SUMMARY

This section provides a general summary of the disclosure, and is not a comprehensive disclosure of its full scope or all of its features.

Disclosed is an imaging system that is operable to acquire one or more image projections of a subject. In various embodiments, the image projections may be acquired and used to reconstruct an image of the subject. In various embodiments, as an alternative and/or in addition thereto, the projections may be viewed directly. The imaging system may include any selected imaging system, such as an x-ray imaging system. Accordingly, in various embodiments, the imaging system may generate a selected energy that is transmitted to and through the subject and is detected by a detector. Accordingly, the emitted energy may be transmitted through one or more filters prior to impinging or reaching the subject.

When acquiring the image data, energy or an energy beam from the imaging system may encounter a filter or material prior to passing through the subject. The material of the filter may alter characteristics of the energy, such as bandwidth, band, dose, or other features of the energy beam. Accordingly, the projections may be acquired of the subject by altering the energy reaching the subject from the source of the imaging system.

A plurality of filters may be positioned in a collimator and moved relative to the subject and the source to acquire a plurality of projections of the subjects with differing energy characteristics. For example, a first projection may be acquired of the subject with no filter and a second projection may be acquired of the subject with a first filter. The two projections may be acquired at the same position of the source and detector, at different positions of the source and detector, or other characteristics. Accordingly, a plurality of projections may be acquired of the subject by altering the energy emitted by the imaging system relative to the subject.

The filters may be moved during an image acquisition series relative to the subject. The image acquisition may be based upon acquiring one or more projections or image data projections through the subject to generate a selected image of the subject. The imaging system may acquire a plurality of projections of a subject with different energy characteristics passing through the subject due to the selection of one or more filters during the acquisition of one or more projections. It is understood, therefore, in addition to the filters that the imaging system may also generate a plurality of different energy characteristics that may also be filtered differently by selected filters.

The imaging system includes a plurality of components, such as a detector and a collimator. The collimator may incorporate or include a source or be positioned relative to a source to collimate the source energy prior to reaching the subject and the detector. The collimator, therefore, may include components and systems to selectively move filters relative to the source and the subject to generate the selected beam toward the subject. The collimator, therefore, may also include control mechanisms to move the filter and/or leaves to shape and/or select characteristics of the energy beam.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6A is a detailed perspective view of a bushing attachment;

FIG. 6B is a side elevation view of the bushing attachment, according to various embodiments;

FIG. 7 is an exploded view of a position sensing assembly;

DETAILED DESCRIPTION

Example embodiments will now be described more fully with reference to the accompanying drawings.

Figure 1:
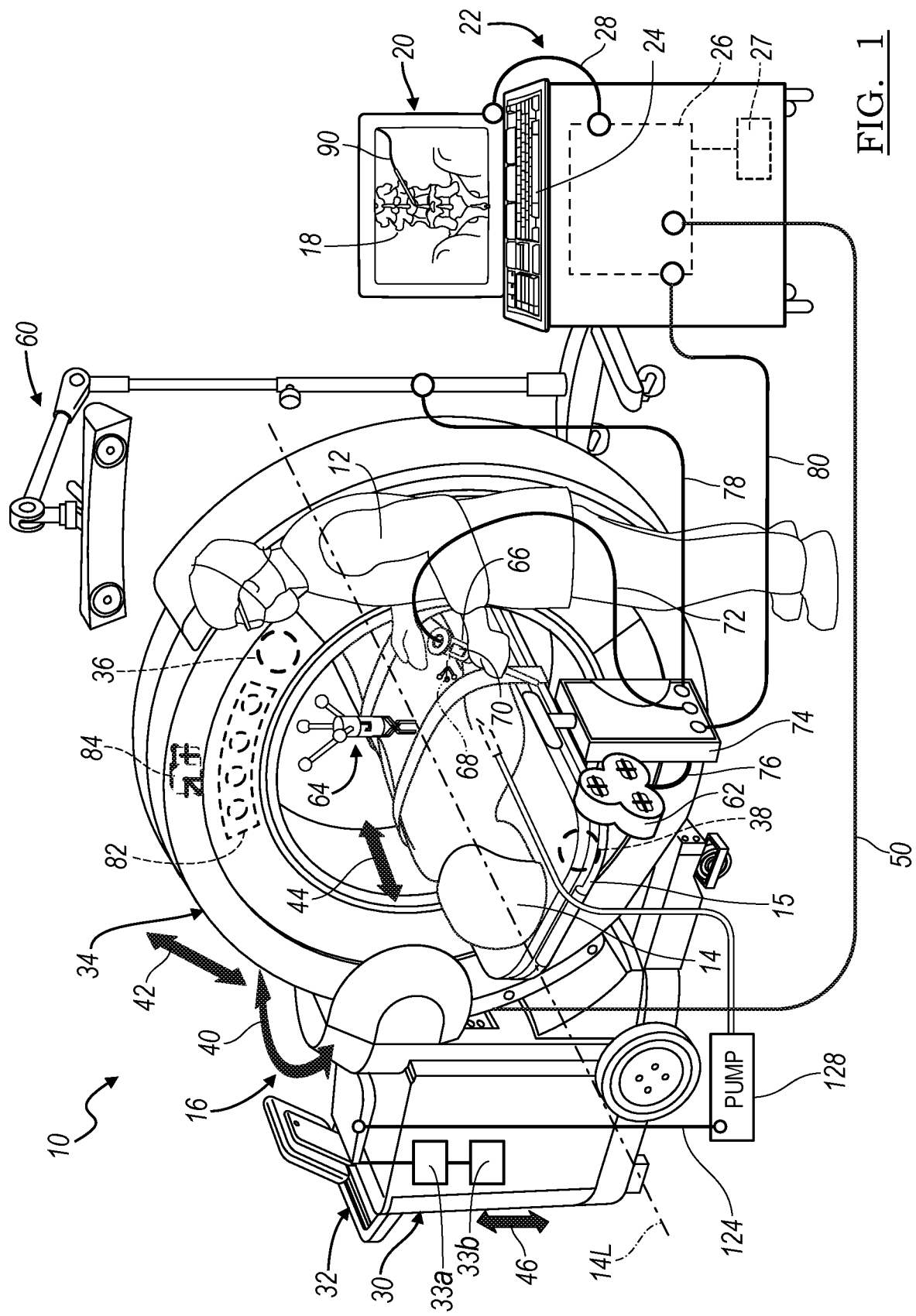
FIG. 1 is an environmental view of an imaging system in an operating theatre.

With reference to FIG. 1, in an operating theatre or operating room 10, a user, such as a surgeon 12, may perform a procedure on a subject, such as a patient, 14. In performing the procedure, the user 12 can use an imaging system 16 to acquire image data of the patient 14 to allow a selected system to generate or create images to assist in performing a procedure. The image data may be generated by power for generating one or more projections of the subject 14. It is understood, however, that various types of image data may be collected and that the various types of image data may be used to generate or reconstruct an image 18.

The image 18 may include a model (such as a three-dimensional (3D) image) that can be generated using the image data and displayed as the image 18 on a display device 20. The display device 20 can be part of and/or connected to a processor system 22 that includes an input device 24, such as a keyboard, and a processor 26 which can include one or more processors or microprocessors incorporated with the processing system 22. The processing system 22 may further include selected types of non-transitory and/or transitory memory 27. A connection 28 can be provided between the processor 26 and the display device 20 for data communication to allow driving the display device 20 to display or illustrate the image 18.

The imaging system 16 may have various portions, such as those of an O-Arm® imaging system sold by Medtronic Navigation, Inc. having a place of business in Louisville, CO, USA. The imaging system 16 may also include and/or alternatively include various portions such as those disclosed in U.S. Patent App. Pubs. 2012/0250822, 2012/0099772, and 2010/0290690, all incorporated herein by reference.

The imaging system 16 may include a mobile cart 30 to allow the imaging system to be mobile. The imagining system 16 may further include a controller and/or control system 32. The control system 32, in various embodiments, may be incorporated into the cart 30 or other appropriate location. Further, the control system 32 may include a processor 33a and a memory 33b (e.g. a non-transitory memory). The memory 33b may include various instructions that are executed by the processor 33a to control the imaging system, including various portions of the imaging system 16.

An imaging gantry 34 of the imaging system 16 may have positioned therein a source unit or system 36 and a detector 38 may be connected to the mobile cart 30. The gantry 34 may be O-shaped or toroid shaped, wherein the gantry 34 is substantially annular and includes walls that form a volume in which the source unit 36 and detector 38 may move. The mobile cart 30 can be moved from one operating theater to another and the gantry 34 can move relative to the cart 30, as discussed further herein. This allows the imaging system 16 to be mobile and moveable relative to the subject 14 thus allowing it to be used in multiple locations and with multiple procedures without requiring a capital expenditure or space dedicated to a fixed imaging system. The processor may include a general purpose processor or a specific application processor and a memory system (e.g. a non-transitory memory such as a spinning disk or solid state non-volatile memory). For example, the memory system may include instructions to be executed by the processor to perform functions and determine results, as discussed herein.

The source unit 36 may be an x-ray source, also referred to as an emitter, that can emit x-rays toward and/or through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move in a 360° motion around the patient 14 within the gantry 34 with the source 36 remaining generally 180° opposed (such as with a fixed inner gantry or moving system) to the detector 38.

The gantry 34 can move isometrically relative to the subject 14, which can be placed on a patient support or table 15, generally in the direction of arrow 40 as illustrated in FIG. 1. The gantry 34 can also tilt relative to the patient 14 illustrated by arrows 42, move longitudinally along the line 44 relative to a longitudinal axis 14L of the patient 14 and the cart 30, can move up and down generally along the line 46 relative to the cart 30 and transversely to the patient 14, to allow for positioning of the source/detector 36/38 relative to the patient 14. The imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc.

The source 36, as discussed herein, may include one or more sources of x-rays for imaging the subject 14. In various embodiments, the source 36 may include a single source that may be powered by more than one power source to generate and/or emit x-rays at different energy characteristics. Further, more than one x-ray source may be the source 36 that may be powered to emit x-rays with differing energy characteristics at selected times.

According to various embodiments, the imaging system 16 can be used with an un-navigated or navigated procedure. In a navigated procedure, a localizer and/or digitizer, including either or both of an optical localizer 60 and an electromagnetic localizer 62 can be used to generate a field and/or receive and/or send a signal within a navigation domain relative to the patient 14. The navigated or navigational space or domain relative to the patient 14 can be registered to the image 18. Correlation, as understood in the art, is to allow registration of a navigation space defined within the navigational domain and an image space defined by the image 18. A patient tracker or dynamic reference frame 64 can be connected to the patient 14 to allow for a dynamic registration and maintenance of registration of the patient 14 to the image 18.

The patient tracking device or dynamic registration device 64 and an instrument 66 can then be tracked relative to the patient 14 to allow for a navigated procedure. The instrument 66 can include a tracking device, such as an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation/probe interface device 74 such as the electromagnetic localizer 62 with communication line 76 and/or the optical localizer 60 with communication line 78. Using the communication lines 74, 78 respectively, the interface 74 can then communicate with the processor 26 with a communication line 80. It will be understood that any of the communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of a tracked location of the instrument 66 relative to the image 18 for performing a procedure.

One skilled in the art will understand that the instrument 66 may be any appropriate instrument, such as a ventricular or vascular stent, spinal implant, neurological stent or stimulator, ablation device, or the like. The instrument 66 can be an interventional instrument or can include or be an implantable device. Tracking the instrument 66 allows for viewing a location (including x,y,z position and orientation) of the instrument 66 relative to the patient 14 with use of the registered image 18 without direct viewing of the instrument 66 within the patient 14.

Further, the gantry 34 can include an optical tracking device 82 and/or an electromagnetic tracking device 84 to be tracked with the respective optical localizer 60 or electromagnetic localizer 62. Accordingly, the imaging device 16 can be tracked relative to the patient 14 as can the instrument 66 to allow for initial registration, automatic registration, or continued registration of the patient 14 relative to the image 18. Registration and navigated procedures are disclosed in U.S. Pat. No. 8,238,631, incorporated herein by reference. Upon registration and tracking of the instrument 66, an icon 90 may be displayed relative to, including superimposed on, the image 18.

Figure 2:
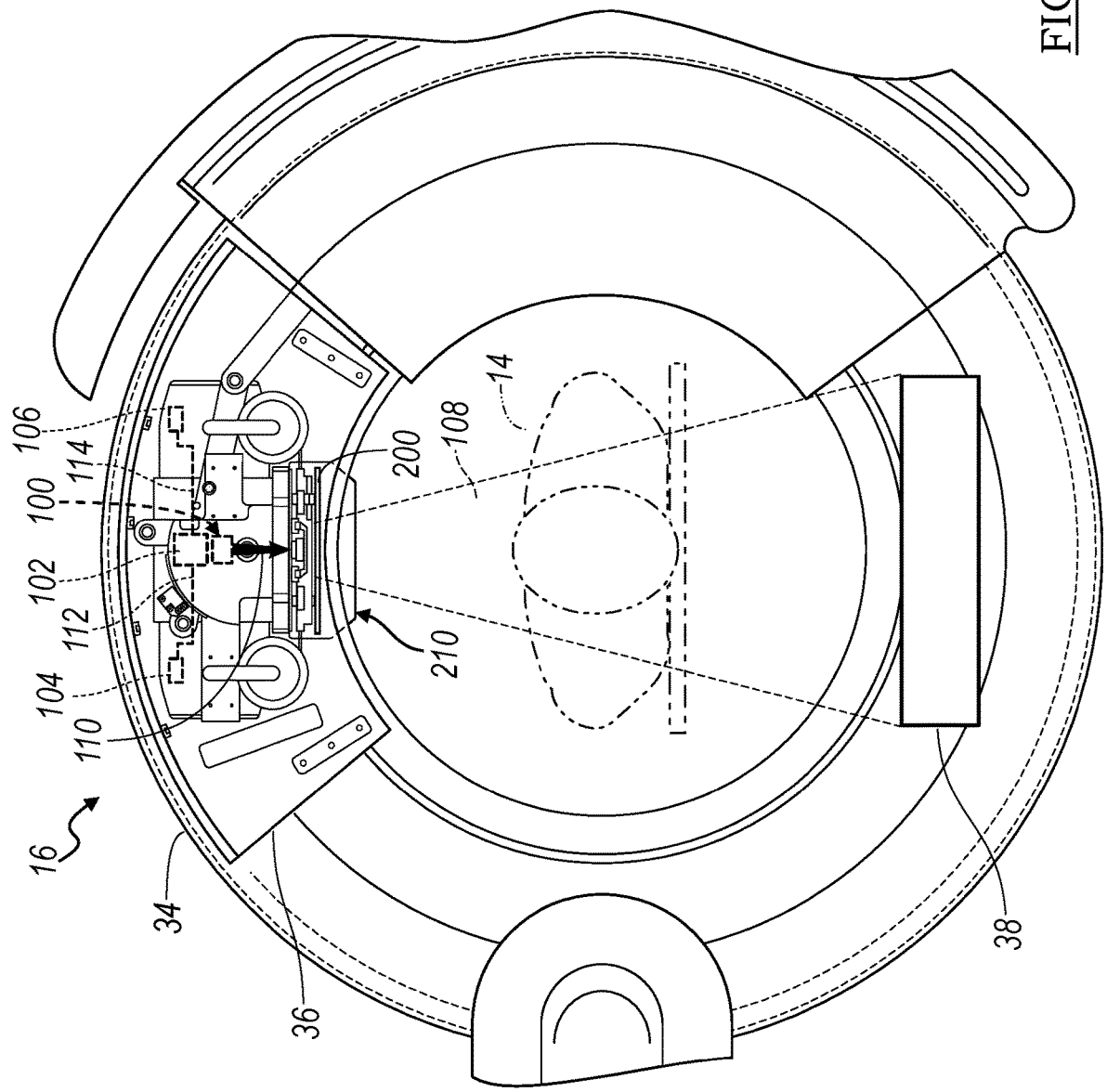
FIG. 2 is a detailed schematic view of an imaging system with a dual energy source system.

Turning reference to FIG. 2, according to various embodiments, the source unit 36 may include various components or features, as discussed herein. For example, the source unit 36 may include a x-ray source such as a single x-ray tube 100 that can be connected to a switch 102 that can interconnect a first power source A 104 and a second power source B 106 with the x-ray tube 100. X-rays can be emitted from the x-ray tube 100 generally in a cone shape 108 towards the detector 38 and generally in the direction from the source 100 as indicated by arrow, beam arrow, beam or vector 110.

The switch 102 can switch between the power source A 104 and the power source B 106 to power the x-ray tube 100 at different voltages and/or amperages to emit x-rays at different energy characteristics generally in the direction of the vector 110 towards the detector 38. The vector 110 may be a central vector or ray within the cone 108 of x-rays. An x-ray beam may be emitted as the cone 108 or other appropriate geometry. The vector 110 may include a selected line or axis relevant for further interaction with the beam, such as with a filter member, as discussed further herein.

It will be understood, however, that the switch 102 can also be connected to a single variable power source that is able to provide power characteristics at different voltages and/or amperages rather than the switch 102 that connects to two different power sources A 104 and B 106. Also, the switch 102 can be a switch that operates to switch a single power source between different voltages and amperages. Further, the source unit 36 may include more than one source, such as x-ray sources, that are each configured or operable to emit x-rays at one or more energy characteristic and or different energy characteristic. The switch, or selected system, may operate to power the two or more x-rays tubes to generate x-rays at selected times.

To acquire a projection, also referred to as an image projection or generally as an image, the patient 14 can be positioned within the x-ray cone 108. Image data of the patient 14 is then acquired at the detector 38 based upon the emission of x-rays in the direction of vector 110 towards the detector 38. Generation of x-ray projections is may be used to collect or acquire image data of the subject for generation of images, as discussed herein.

The two power sources A and B 104, 106 can be provided within the source unit 36. Alternatively, or in addition therefore, the powered sources 104, 106 can be separate from the source unit 36 and simply be connected with the switch 102 via appropriate electric connections such as a first cable or wire 112 and a second cable or wire 114. The switch 102 can switch between the power source A 104 and the power source B 106 at an appropriate rate to allow for emission of x-rays at two different energies through the patient 14 for various imaging procedures, as discussed further herein. The differing energies can be used for material separation and/or material enhanced reconstruction or imaging of the patient 14.

The switching rate of the switch 102 can include about 1 millisecond (ms) to about 1 second, further including about 10 ms to 500 ms, and further including about 50 ms. According to various embodiments, the power may be switched at a rate of about 30 Hz. Thus, x-rays may be emitted with energy characteristics according to each power source A and B for about 33 ms.

Further, the power source A 104 and the power source B 106 can be provided to include different power characteristics, including different voltages and different amperages, based upon selected contrast enhancement requirements. The different power characteristics allow the x-rays to include different energy characteristics. The differing energy characteristics of two or more different x-rays emissions interact and are attenuated (e.g. absorbed, blocked, deflected, etc.) by the same material differently. For example, as discussed further herein, different energy characteristics can be selected to allow for contrast enhancement (e.g. enhanced viewing and identification) between soft tissue (e.g. muscle or vasculature) and hard tissue (e.g. bone) in the patient 14, that may be done without any contrast agent present. Also, differing energy characteristics may assist in increasing contrast between a contrast agent injected or provided to the patient 14 through an injection or provision pump 120 that may be controlled by the image controller 32 (or other appropriate control system) in the patient 14 and an area without a contrast agent injected in the patient 14.

As discussed further herein, each emission of x-rays at a selected energy characteristic may include a x-ray energy spectral range. The x-ray energy spectral range for any given powering level, however, may be generally broad. Broad, for example, may include a range of energies at which x-rays are emitted and not only at a specific and/or single energy level. Thus, even if two different powering characteristics are used, emitted x-rays may overlap between two emissions of x-rays generated with the two power sources A and B. A filter assembly 150 may include a filter member of a filter material, as discussed herein, which may be used to attenuate some of the spectra of one or more of an emission of x-rays. In attenuating part of a spectrum of an emission of x-rays, differentiation between two emissions may be greater and spectral overlap may be minimized. For example, the filter member may attenuate lower energy x-rays from when the x-ray tube is powered by the higher powered power source A or B. The source unit 36 may be referred to as a collimator and/or the filter assembly may be incorporated into a collimator assembly, as discussed herein.

As an example, the power source A 104 can have a voltage of about 75 kV and can have an amperage of about 50 mA, which can differ from the power source B which can have a voltage of 150 kV and 20 mA. The selected voltages and amperages can then be switched with the switch 102 to power the x-ray tube 100 to emit the x-rays with selected energy characteristics generally in the direction of the vector 110 at and/or through the patient 14 to the detector 38. It will be understood that the range of voltages for the power source A may be about 40 kV to about 80 kV and the amperages can be about 10 mA to about 500 mA. Generally, the power characteristic differences between the first power source A 104 and the second power source B 106 can be about 40 kV to about 60 kV and about 20 mA to about 150 mA. In other words, for example, the power source B may power the x-ray tube 100 at a voltage that is about 40 kV to about 60 k V and an amperage that is about 20 mA to about 150 mA greater than power source A. In addition to the energy and mA difference, the pulse width of the exposure may be varied as well from 1 ms to 50 ms.

The dual power sources allow for dual energy x-rays to be emitted by the x-ray tube 100. As discussed above, the two or dual energy x-rays can allow for enhanced and/or dynamic contrast reconstruction of models of the subject 14 based upon the image data acquired of the patient 14. It is understood, however, that more than two power sources may be provided or they may be altered during operation to provide x-rays at more than two energy characteristics. The discussion herein of two or duel energy is merely exemplary and not intended to limit the scope of the present disclosure, unless specifically so stated.

It is understood, however, that the imaging system may also be used to generate projections with a single power. Thus, a single or dual power imaging system may be used to generate image data projections. The projections, regardless of how they are collected, may be used to generate images.

The images 18 may be generated by reconstruction from the image data. In various embodiments, an iterative or algebraic process can be used to reconstruct the image 18. The image 18 may include a model of at least a portion of the patient 14 based upon the acquired image data. It is understood that the model may include a three-dimensional (3D) rendering of the imaged portion of the patient 14 based on the image data. The rendering may be formed or generated based on selected techniques, such as those discussed herein.

The power sources can power the x-ray tube 100 to generate two dimension (2D) x-ray projections of the patient 14, selected portion of the patient 14, or any area, region or volume of interest. The 2D x-ray projections can be reconstructed, as discussed herein, to generate and/or display three-dimensional (3D) volumetric models of the patient 14, selected portion of the patient 14, or any area, region or volume of interest. As discussed herein, the 2D x-ray projections can be image data acquired with the imaging system 16, while the 3D volumetric models can be generated or model image data.

For reconstructing or forming a 3D volumetric image, appropriate algebraic techniques include Expectation maximization (EM), Ordered Subsets EM (OS-EM), Simultaneous Algebraic Reconstruction Technique (SART) and Total Variation Minimization (TVM), as generally understood by those skilled in the art. The application to perform a 3D volumetric reconstruction based on the 2D projections allows for efficient and complete volumetric reconstruction. Generally, an algebraic technique can include an iterative process to perform a reconstruction of the patient 14 for display as the image 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the model or the image data 18 can be built based upon image data acquired of the patient 14 with the imaging device 16.

The projection image data may be 2D projections and may be acquired by substantially total or partial annular or 360° orientation movement of the source/detector 36/38 around the patient 14 due to positioning of the source/detector 36/38 moving around the patient 14 in the optimal movement. An optimal movement may be a predetermined movement of the source/detector 36/38 in a circle alone or with movement of the gantry 34, as discussed above. An optimal movement may be one that allows for acquisition of enough image data to reconstruct a select quality of the image 18. This optimal movement may allow for minimizing or attempting to minimize exposure of the patient 14 and/or the user 12 to x-rays by moving the source/detector 36/38 along a path to acquire a selected amount of image data without more or substantially more x-ray exposure.

Also, due to movements of the gantry 34, the detector need never move in a pure circle, but rather can move in a spiral helix, or other rotary movement about or relative to the patient 14. Also, the path can be substantially non-symmetrical and/or non-linear based on movements of the imaging system 16, including the gantry 34 and the detector 38 together. In other words, the path need not be continuous in that the detector 38 and the gantry 34 can stop, move back the direction from which it just came (e.g. oscillate), etc. in following the optimal path. Thus, the detector 38 need never travel a full 360° around the patient 14 as the gantry 34 may tilt or otherwise move and the detector 38 may stop and move back in the direction it has already passed.

In acquiring image data at the detector 38, the emitted energy, including in various embodiments, dual energy x-rays generally interact with a tissue and/or a contrast agent in the patient 14 differently based upon the characteristics of the tissue or the contrast agent in the patient 14 and the energies of the two x-rays emitted by the x-ray tube 100. For example, the soft tissue of the patient 14 can absorb or scatter x-rays having an energy produced by the power source A 104 differently than the x-rays having energy produced by the power source B 106. Similarly, a contrast agent, such as iodine, can absorb or scatter the x-rays generated by the power source A 104 differently from those generated by the power source B 106. Switching between the power source A 104 and the power source B 106 can allow for determination of different types of material properties (e.g. hard or soft anatomy or between two types of soft anatomy (e.g. vessels and surrounding tissue)), contrast agent, implants (e.g. metal implants) and surrounding natural anatomy (e.g. bone), or etc. within the patient 14. By switching between the two power sources 104, 106 and knowing the time when the power source A 104 is used to generate the x-rays as opposed to the power source B 106 to generate the x-rays the information detected at the detector 38 can be used to identify or segregate the different types of anatomy or contrast agent being imaged.

A timer can be used to determine the time when the first power source A 104 is being used and when the second power source B 106 is being used. This can allow the images to be indexed and separated for generating different models of the patient 14. Also, as discussed herein, the timer, which can be a separate system or included with the imaging system 16 or the processor system 26, can be used to index image data generated with the contrast agent injected into the patient 14.

At least because the x-ray tube 100 is in a moveable imaging system, such as the imaging system 16, it can be moved relative to the patient 14. Thus, the x-ray tube 100 may move relative to the patient 14 while the energy for the x-ray tube 100 is being switched between the power source A 104 and the power source B 106. Accordingly, an image acquired with the power source A 104 may not be at the same pose or position relative to the patient 14 as the power source B 106. If the model is desired or selected to be formed of a single location in the patient 14, however, various interpolation techniques can be used to generate the model. Interpolation may between image data acquired at a first time and image data acquired at a second time. The image data at the first and second times may be generated with the two different energies. Thus, the model may be formed including image data from both energies using interpolation between the acquired image data. Further, the interpolation may be to account for an amount of movement (e.g. linear, rotational, etc.) of the x-ray tube 100 between when the projection with the power source A 104 and the projection with the power source B 106 was acquired.

The dual energy of the x-rays emitted by the x-ray tube 100 due to the two power sources 104, 106 can allow for substantially efficient and enhanced contrast discrimination determination between the vasculature and the musculature of the patient 14. Moreover, the switching by a switch 102 between the power source A 104 and the power source B 106 allows for an efficient construction of the source 36 where the single x-ray tube 100 can allow for the generation of x-rays at two different energies to allow for enhanced or dynamic contrast modeling of the patient 14, such as modeling the vasculature of the patient 14 including a contrast agent therein.

Duel energy imaging systems may include those disclosed in U.S. Pat. App. Pub. Nos. 2012/0099768 and 2012/0097178, both incorporated herein by reference.

In addition to the generation of x-rays of different energies, including dual energy x-rays as discussed above, the filter assembly 200 can be used to assist in insuring or creating a select differentiation between x-ray spectras of x-rays of the two different energies prior to x-rays reaching the detector 38. The filter assembly 200 can also be timed in conjunction with the switching the x-ray energies, with the switch 102, injection a contrast agent with the pump 120, or other appropriate timing. Therefore, the filter assembly 200 can be operated to image the patient 14 to achieve the differentiation between the dual energies of the x-rays.

Figure 3:
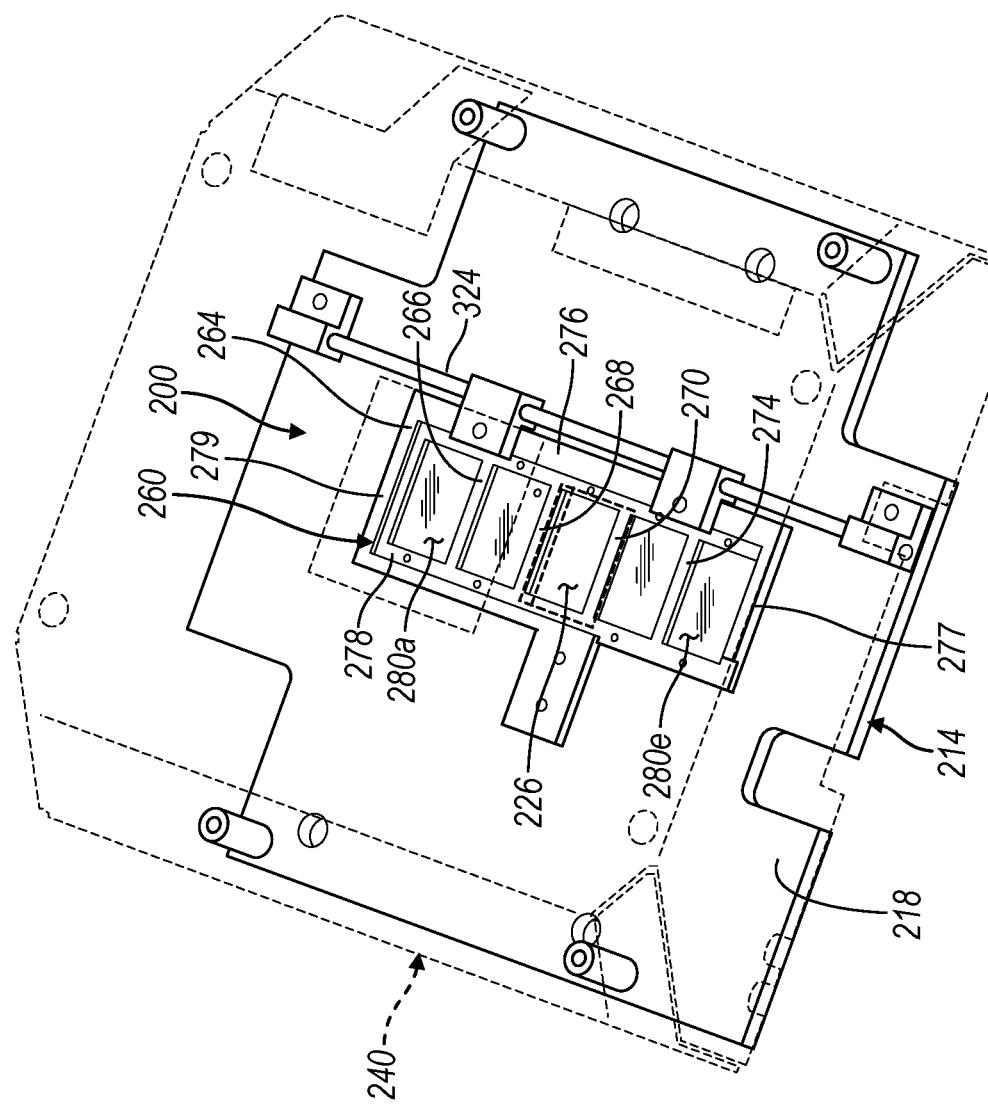
FIG. 3 is a top perspective view of a collimator assembly.

Turning reference to FIG. 3, a selected portion of the unit 36 may include or have positioned relative thereto a collimator assembly 210. The collimator assembly 210 may include the filter assembly 200. It is understood that selected filter assemblies may be used, such as those discloses in U.S. Pat. App. Pub. No. 2018/0310900, incorporated herein by reference. The filter assembly 200 includes various components, as discussed herein.

The collimator 210 may include various components, such as the filter assembly 200, as discussed further herein, that may be movably connected or interconnected with a base or mounting plate 214. The mounting plate 214 may have a source facing side 218 and a patient or subject facing side 222. The mounting plate 214 may further define an aperture 226 that extends through the mounting plate 314.

On the patient facing side 222 various rings or covers may be mounted such as an aperture cover 230 and an aperture feature or portion 234. The aperture ring or portion 234 may be formed of a selected material, such as lead or other x-ray impervious material. Accordingly, for imaging the subject 14, substantially all of the x-ray beam 108 may extend or pass through the aperture 226 and extraneous portions would be blocked by the ring 234.

Further, mounted to the mounting place 214 may be an axis selecting assembly 240. The axis selecting assembly 240 may include various portions or leaves that may move relative to the source 100 to move or direct a portion of the beam 108 through the aperture 226. The axis selecting assembly 240 may be any appropriate type of axis selecting assembly such as that included in the O-arm® Imaging System, sold by Medtronic, Inc. and/or that disclosed in U.S. Pub. No. 2018/0310900, incorporated herein by reference. The axis selecting assembly 240 may select an area smaller than the full area of the aperture 226, including a selected portion or region of the aperture 226 through which x-rays may pass. The x-rays may be filtered by the filter assembly 200, as discussed further herein. However, the specific selection of an axis or aperture addition and/or size may be performed according to any appropriate aperture selection assembly. Accordingly, the axis selection assembly 240 will not be described in detail here, as an appropriate one is understood by one skilled in the art.

Figure 4:
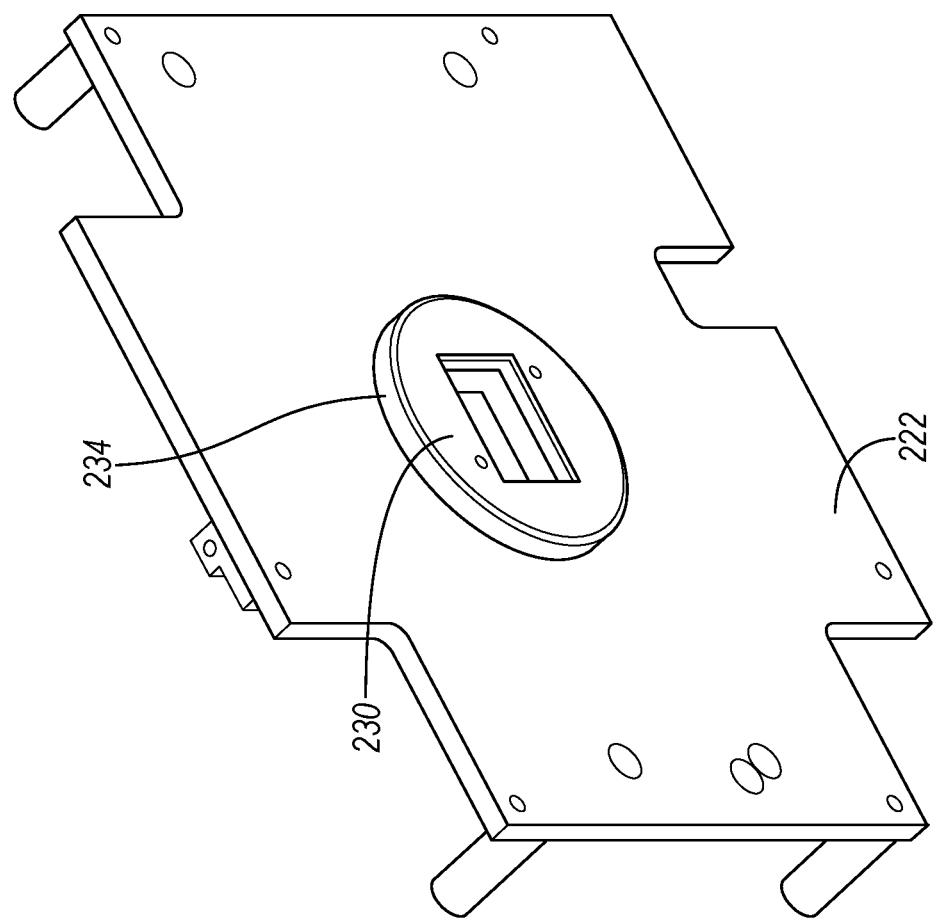
FIG. 4 is a bottom perspective view of a collimator assembly of FIG. 3.

The filter assembly 200 is illustrated in detail in FIG. 5 and will be discussed herein with greater detail with continuing reference to FIG. 3 and FIG. 4. The filter assembly 200 may include various components that may be fixedly mounted and/or movably coupled to the mounting plate 214. For example, the mounting place 214 may include stand off or spacers 246 that allow for positioning of the axis selection assembly 240 spaced away from the mounting plate 214. The filter assembly 200, therefore, may be positioned in the space or volume defined between the mounting plate 214, such as the source facing side 218, and the axis selection assembly 240. In various embodiments, therefore, the filter assembly 200 may exist in a volume or are that has a height that may be substantially equivalent or the same as a height 250 of the spacers 246. It is understood, however, that various portions of the filter assembly 200 may extend out from the mounting plate 214 and, therefore, have a dimension greater than the height 250 of the spacers 246.

The mounting plate 214 may act as a mounting plate or base for various components, as discussed above. In particular, the mounting plate 214 may allow for mounting and moving of the filter assembly 200. The filter assembly 200 may include various components, such as a ladder frame or ladder member 260. The ladder member 260 may include an outer frame or boundary portion 264 and one or more cross members, such as four cross members 266, 268, 270, 274 extending between two elongated or side members 276, 278. The side members 276, 278 with end cross-members 279 may form the boundary portion 264. The cross members 266-274 in combination with the boundary portion 264 can form or define a plurality of openings or filter areas 280a-280e.

The filter areas 280*a*-280*e* may have selected filter materials and/or open spaces formed or positioned relative thereto to allow for filtering the beam 108 from the source 100, as discussed further herein. In various embodiments, the filter frame 260 may have a plurality of filter members or materials mounted or fixed thereto such as a copper member 282, a lead member 284, and open position 286, a slotted filter 290, and an alternative or additional position 294. It is understood that any appropriate materials may be positioned in the ladder frame 260 to form the filter portions of the filter assembly 200, and the materials noted above are merely exemplary. Moreover, the ladder frame 260 may move relative to the aperture 226, as discussed further herein, to position selected one or more of the filter member or portions 282-294 between the source 100 and the aperture 226. Accordingly, the ladder frame 260 may be used to position selected filter materials or areas to filter the beam 108 relative to the subject 14.

The mounting plate 214 may have various components fixed thereto that may associated and/or allow or selectively determine or limit operation of the filter frame 260. For example, the filter frame 260 may have a mounting location or projection 300. The projection 300 may be used to mount various components to the filter frame 260, as discussed further herein.

In various embodiments, the frame 260, and/or a portion thereof may contact a first stop 310 and a second stop 314. In various embodiments, the projection 300 may contact one or more stops or limiters 310, 314. The stops may be formed of extruded and machined material, such as aluminum. Generally, the stops may have a mounting plate engaging portion 313 and a frame engaging portion 315. The frame engaging portion 315 may be substantially flat or planar.

The stops 310, 314 may be fixed to the mounting plate 214 in any appropriate manner such as with fasteners 318. The fasteners 318 may be appropriate fasteners such as bolts, screws, rivets, or the like. Additionally, or alternatively thereto, selected snap fits, adhesives, or the like may be used to fix the stops 310, 314 to the mounting plate 214. It is understood, however, that the stops 310, 314 may also be formed integrally as a single piece or portion with the frame plate 214. For example a portion of the plate 214 may be cut and bent to act as the stop, such as either or both of the stops 310, 314.

The filter frame 260 may move relative to the mounting plate 214 and the projection 300 may engage the stops 310, 314 at selected limited or end limits of movement of the filter frame 260. The stops 310, 314 may limit movement of the frame 260. Further, the stops may operate to indicate a final position or a selected position, such as a home position, of the frame 260. The position of the filter members relative to the frame 260 are known and, therefore, relative to any position of the frame 260. The position of the frame relative to the plate 214, including the aperture 226, may be, therefore, know with the stops and as discussed herein.

The frame 260 may be movably connected to a rail 324. The rail 324 may be fixed to the mounting plate 214 in any appropriate manner, such as with rail mounts, including a first rail mount 326 and a second rail mount 328. In various embodiments, the filter assembly 200 may include only the single rail 324.

The two rail mounts 326, 328 may be fixed to the mounting plate 214 in an appropriate manner, such as with selected fasteners including a fastener 330. The fastener 330 may be a screw, bolt, rivet, or other appropriate fastener.

Further, as discussed above, selected adhesives or snap fits may be used to fasten the mount 326, 328 to the mounting plate 214.

The mounts 326, 328 may include opposed bores or through bores that receive respective ends of the rail 324. The rail 324 may, therefore, be fixed to the mounting plate 214 in a selected position. As exemplarily illustrated in FIG. 5, the rail 324 may be fixed at a selected position relative to the aperture 226.

Figure 5:
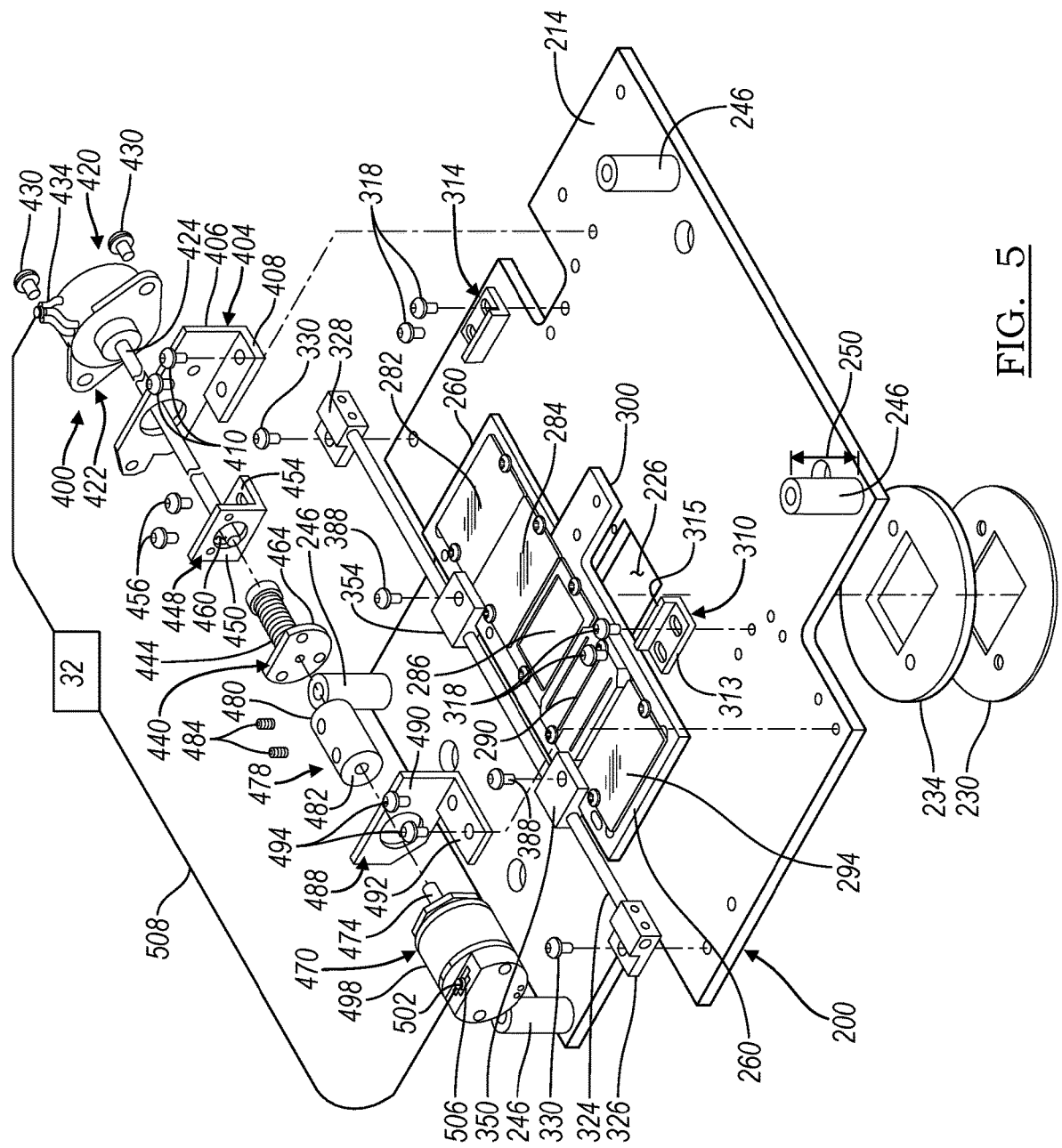
FIG. 5 is a detailed view of a filter selection assembly, according to various embodiments.

With continuing reference to FIG. 5 and additional reference to FIG. 6, the frame 260 is mounted to or connected to one or more bushings, such as a first busing 350 and a second bushing 354. It is understood that any appropriate number of bushings may be provided and discussion of only two bushings, here, is merely for clarity of the current discussion. Further, two bushings may be provided to minimize or eliminate rotation of the frame 260 relative to the rail 324 and/or the aperture 226. It is understood that additional bushings may also be provided to assist in reducing or eliminating rotation. Further, a single bushing of a selected size may also be provided to provide appropriate stability of the frame 260 relative to the rail 324.

With continuing reference to FIGS. 6A and 6B, the bushing 350 will be described in greater detail. The bushing 350 may be substantially identical to the bushing 354, and therefore a repetitive discussion will not be provided of the second bushing 354. Nevertheless, the bushing 350 may include a rail engaging portion 360 that may include or define a throughbore 364. Accordingly the bushing 350 may move along, e.g. slide along, the rail 324, as discussed further herein. Further the bushing 350 may include a frame engaging portion or region 368.

The frame engaging region 368 may include a first engaging surface or portion 372 and a second surface or engaging portion 376. The two engaging surfaces or portions 372, 376 may be formed at an angle 382 relative to one another. For example, the angle 382 may allow the bushing 354 to register to the frame 260 at a selected position relative to the frame 260. For example, the side rail or extension 276 may be received into the frame engaging portion 368 due to the two surfaces 372, 376 as substantially a single or only position or orientation relative to the bushing 350. Thus, the bushing 350 may be registered or positioned relative to the frame 260 at substantially a single position. It is understood, as noted above, that the bushing 350 may be positioned in any appropriate location relative to the frame 260, such as positioned relative to the filter position 280.

Once the bushing 350 is registered relative to the frame 260 it may be fixed or mounted to the frame 260. For example, a fastener 388 may engage the frame 260. The fastener 388 may include a screw, bolt, rivet, or the like that passes through a bore 392 of the bushing 350 and engages the frame 260, such as along or on the beam 276. Accordingly, the frame 260 may be mounted to the bushing 350 which is movable relative to the rail 324, such as in a sliding manner.

By mounting the frame 260 to the bushing 350, the frame 260 may move along the rail 324. Movement of the frame member 260 relative to and/or along the rail 324 allows for selected filter members or positions to be positioned relative to the aperture 226, such as over the aperture between the subject 14 and the source 100. As discussed further herein, movement of the frame member 260, such as along the rail 324, allows for positioning selected portions of individual filters and/or selected filters over the aperture 226.

As discussed above, the frame 260 may move relative to the mounting plate 214 relative to the rail 324. The rail 324 may be formed of any appropriate material such as extruded aluminum, stainless steel, titanium, or any appropriate material. Generally, the rail 324 is formed of a material that is hardened and will not flex during use including movement of the frame member 260. The frame member 260, therefore, may be moved relative to the aperture 226, such as being slid along the rail 324 by cooperating with the bushing 350, 354 with a selected motion system 400.

The motion system 400, with continuing reference to FIG. 5, may include various components or assemblies. The components may be mounted to the mounting plates 214 in an appropriate manner, such as with a motor mounting bracket or member 404. The motor mounting bracket 404 may include a motor mounting portion 406 and a plate mounting or connection portion 408. The mounting bracket 404 may be fixed to the fixture plate 214 with one or more fasteners, such as fasteners 410. The fasteners 410 may be any appropriate fasteners such as screws, bolts, rivets, or other appropriate fasteners. Additionally, the bracket 404 may be fixed to the plate 214 with one or more adhesives. Also, as discussed above, the bracket 404 may be formed integrally with the plate 214 such as by cutting and bending a portion of the plate 214.

The mounting bracket 404 may allow for fixation of one or more motors 420. The motor 420 may be any appropriate motor such as an electric motor with selected windings, such as including a stepper motor. The motor 420 may be configured to operate at a selected voltage, such as about 5 volts (V). The motor may form a portion of an actuating assembly 422 with a screw 424. Selected actuators may include a Haydon® Kerk™ actuator sold by Haydon Kerk Motion Solutions, Inc. have a place of business in Connecticut, USA.

The actuator screw 424 may be rotated by the motor 420 of the actuator assembly 422. The motor 420 may be mounted to the bracket 404 in any appropriate manner, such as with one or more fasteners 430. The fasteners may be any appropriate fasteners, such as those discussed above. Additionally, the motor 420 may be mounted to the bracket 404 with any appropriate mechanism, such as adhesives, or the like. Further, the motor 424 may be powered by selected control systems that may be connected to the motor 420 with selected connections 434. The connections 434 may connect to the imaging system controller 32, as discussed above. Accordingly, the actuator assembly 422 may be operated and/or controller by the image controller 32 to acquire image data or projections of the subject 14 as discussed further herein.

The actuator assembly 422 may rotate the screw 424 at an appropriate rate. For example, the screw 424 may be a threaded screw that has a selected pitch. For example, the screw 424 may include a pitch of any selected amount such as causing axial movement of the frame 260 along the rails 324 per rotation of the screw 424. For example the screw 424 may include a pitch that causes about 0.005 inches of axial movement per revolution (about 0.1 millimeters per revolution (mm/rev) to about 0.1 in/rev (about 2.5 mm/rev), including about 0.01 in/rev (about 0.3 mm/rev) to about 0.05 in/rev (about 1.3 mm/rev), further including about 0.024 in/rev (about 0.61 mm/rev). The axial movement may generally be of the frame 260 along the rail 324 and the revolution is per one single rotation (i.e. rotation of 360 degrees) of the screw 424. The motor may be a stepper motor and have a step that is about 7.5 degrees. Thus, a full step of the motor 420 may create movement of about 0.0001 inches (about 0.003 mm) to about 0.01 inches (about 0.3 mm), including about 0.003 inches (about 0.08 mm) to about 0.007 inches (about 0.2 mm) per full step, and further including about 0.0005 inches (about 0.01 mm). Accordingly, the actuator assembly 422 may selectively move the frame 260 by being connected thereto, as discussed herein in an appropriate amount per rotation of the screw 424.

As discussed above, the motor 420 of the actuator assembly 422 may be fixed to the bracket 404 that is fixed to the plate 214. The actuator 422 includes the screw 424 that may extend from the motor 420 and engage a nut assembly 440. The nut assembly 440 may be connected to the screw 424 in any appropriate manner. The nut 440 may include a nut such as that incorporated into or included with Haydon® Kerk™ 26000 series actuators sold by Haydon Kerk Motion Solutions, Inc. have a place of business in Connecticut, USA.

The nut 440 may include selected features such as an anti-backslash portion that may include a resilient member, such as a spring 444. The nut 440 may be mounted to a nut bracket 448 that includes a nut mounting portion 450 and a frame mounting portion 454. The frame mounting portion 454 may be fixed to the frame 260, such as at the projection 300, with one or more fasteners, including the fasteners 456. The fasteners 456 may be any appropriate fasteners, such as those discussed above. Additionally, the nut bracket 448 may be fixed to the frame 260 with selected adhesives or other appropriate portions. Further, as discussed above, the nut bracket 448 may be integral with the frame 260, such as forming the projection 300 in an appropriate manner to receive or engage the nut 440.

In various embodiments, the nut bracket 448 includes a passage or throughbore 460 through which a portion of the nut 440, such as the anti-backslash portion 444 may then pass through. The nut 440 may include a mounting flange 464 that may be fixed to the nut engaging portion 450 in an appropriate manner, such as with fasteners or adhesives as noted above.

Regardless of the fixation of the nut 440 to the bracket 448, the rotation of the screw 424 may cause movement of the bracket 448 due to engagement of the nut 440 to the bracket 448 and the nut 440 to the screw 424. Further, movement of the bracket 448 may cause movement of the frame 260 due to engagement of the nut bracket 448 to the projection 300, according to various embodiments. Thus, movement of the screw 424 of the actuator 422 may cause movement of the frame 260.

As discussed herein, the actuator 422 may be operated with the image system controller 32 or any appropriate controller. The actuator 422 may be operated according to instructions to position a selected filter at the aperture 226 or to move the frame 260 to a selected position relative to the aperture 226. Accordingly, the frame 260 may be moved due to the actuator 422 by powering and controlling the motor 420 to rotate the screw 424 that is connected to the nut 440.

The actuator assembly 422 may be coupled to an encoder assembly 470. In various embodiments, the screw 424 is connected with the nut assembly 440, as discussed above, and may be further coupled to an input shaft or encoder shaft 474 of the encoder assembly. The screw 424 may be coupled to the shaft 474 with a selected coupler, such as a coupler assembly 478. The coupler assembly 478 may receive the screw 424 at a first end 480 and the shaft 474 at a second end 482. The screw 424 and the shaft 474 may have the same or substantially same diameter (such as within about 10% of each other). Thus, the coupler 478 may have a single internal diameter and no step. Selected fixation members, such as one or more set screws 484 may be used to fix the respective screw 424 and shaft 474 within or to the coupler 478.

The encoder assembly 470 may be fixed to an encoder bracket 488. In various embodiments, the bracket 488 may be formed from extruded aluminum and bent and/or machined to a selected size and shape. The encoder bracket 488 may include an encoder connecting portion 490 and a plate connection portion 492. The plate connection portion 492 may be fixed to the mounting plate 214 with appropriate fasteners, such as fasteners 494. As noted above, the fasteners 494 may be any appropriate fasteners and/or additional or alternative fixation means or mechanisms may be used to fix the bracket 488 to the plate 214. Also, as noted above, the bracket 488 may be formed integrally with the plate 214, such as being formed as a portion thereof and bent to engage the encoder assembly 470.

The encoder assembly 470 may include various portions, such as the input or encoder shaft 474 and discussed in greater detail herein and illustrated in FIG. 7. The shaft 474 may extend through an encoder housing 498. The shaft 474 may then interact with an encoder module 502 in an appropriate manner. In various embodiments, the shaft 474 and/or portions connected thereto may provide an input to the encoder module 502.

For example, the encoder module 502 may include a magnetic encoder. Selected magnetic encoders may include non-contact magnetic encoder module where a magnet is fixed to the shaft 474 and rotates relative to a sensor as a part of the encoder module 502. In various embodiments, the encoder may include a sensor, such as a Hall effect sensor, to sense movement and/or positions of magnetic fields, such as those produced by a magnetic. The encoder module 502 may include a Renishaw® RMB20 magnetic encoder module sold by Renishaw, having a place of business in Gloucestershire England. Other appropriate types of encoders may include optical and capacitive. Encoders may include the AR18 series sold by Broadcom, Inc. having a place of business at San Jose, Calif. or the E6A2-C encoder sold by OMRON Corporation having a place of business at Hoffman Estates, IL.

Regardless of the media used for the encoding by the encoder, encoders may also include an incremental or an absolute. An incremental encoder may counts pulses (e.g. during movement), but does not know where it is in space. An incremental encoder is "homed" to establish a zero position. A home position may be determined such as by a hard stop, as discussed in various embodiments herein. An index pulse is established inside the encoder to occur once per rotation and provides a reliable location. In various embodiments, the absolute encoder may also and/or alternatively be used and knows where it is at all times.

The encoder module 502, therefore, may sense rotation of the shaft 474. Rotation of the shaft 474 may be read out or measured due to the change in magnetic fields formed by a magnet that is fixed to the shaft 474. The shaft 474 may rotate due to rotation of the screw 424 being coupled to the shaft 474 with the couple assembly 478. The encoder bracket 488 and the actuator bracket 404 assist in ensuring that the actuator assembly 422 and the encoder assembly 470 are substantially fixed relative to the plate 214 and/or to each other. The actuator 422, therefore, may move the frame 260 relative the mounting plate 214 by actuation of the screw 424. Rotation of the screw 424, when moving the frame 260, then rotates the encoder shaft 474 due to the coupling assembly 478. Thus, the encoder assembly 470, including the encoder module 502 may be used to generate a signal regarding rotation of the encoder shaft 474.

Further, the encoder assembly 470, including the shaft 474, are inline with the screw 424. Moreover, the encoder shaft is connected to the screw 424 at a position distal from the motor 420. Thus, twisting or torsional motion in the screw 424 may be accounted for by the encoder when determining movement of the frame 260. The connection to the screw 424, particularly when in line therewith, allows the encoder to confirm and/or determine actual movement fo the screw 424. As the screw 424 is connected to the frame 260, the frame 260 moves when the screw 424 rotates. Although the motor 420 may be driven or commanded (e.g. with a selected number of pulses) to move the screw 424, the screw 424 may not move for various reasons. The screw 424 and/or the motor 420 may not rotate due to friction, obstructions, etc. The encoder 420 being connected to the screw 424 may measure and/or determine actual movement of the screw 424. Thus, the encoder 470 may be used to confirm the motor 420 moved the desired distance, and a motion controller of the motor 420 can detect an error in the move distance, if present, and add additional increment step commands to insure the motor 420 and/or screw 424 and/or frame 260 moves the desired distance.

As discussed herein, the encoder module 502 may include a connection 506. The connection 506 may allow a communication connection 508 to be made to a selected module or processor system, such as the image controller 32. The image controller 32 may receive and/or transmit a signal with the communication line 508 to the encoder module 502. In various embodiments, for example, the encoder module 502 may transmit a signal based upon the rotation of the encoder shaft 474 to the image controller 32. The image controller 32 may also transmit and/or receive a signal to the motor 420 of the actuator assembly 422. Accordingly, the image controller 32 may transmit and/or receive signals regarding movement of the frame 260. Thus, the image controller 32 may be used to move the frame 260 in a known and selected manner due to the actuator assembly 422 and/or the encoder assembly 470. It is understood, however, that any appropriate processor system may be used to control the actuator assembly 422 and/or receive a signal from the encoder assembly 470. The image controller 32 is merely exemplary as discussed herein. Further, it is understood that the communication lines 508, 434 may be any appropriate type of communication, as also discussed herein. Communication 434, 508 may be wired, wireless, transmission due to access to a communication or data storage network, or the like.

Further, as illustrated in FIG. 5, the rail 324 is opposite the frame 260 from the screw 424. Thus, the screw 424 may apply a force on a first side of the frame 260 and the rail is interconnected with the frame 260 on a second side. In various embodiments, as illustrated, the filter assembly 200 may include only the single rail and the single screw 424. The screw 424 may also be alternatively referred to as drive or worm screw. The actuator 422 may also be referred to as a movement or drive system with the rail 324.

The screw 424 and the encoder shaft 474 are generally linearly aligned with one another. In various embodiments, the screw 424 and the encoder shaft 474 rotate around a common axis. The coupler 478 is also generally in the same axis and axially fixes the screw 424 relative to the encoder shaft 474. The stops 310, 314 may be generally aligned and placed in plane with the axis of the screw 424.

With continuing reference to FIG. 5 and additional reference to FIG. 7, the position determining assembly 470 is described in greater detail. As noted above, the position determining assembly 470 includes the positioning determining module or encoder module 502. The position determining encoder 502 may include any appropriate encoder, such as that discussed above. Generally the encoder 502 may sense rotating magnetic fields of a magnet 520. The magnet 520 may generate magnetic poles that are sensed by a sensor incorporated in the encoder module 502. The magnet 502 may be fixed to the encoder shaft 474. In various embodiments, the encoder shaft 474 may include a first end, such as substantially first terminal end 524 that includes an engaging or capturing region 526. The magnet 520 may be fixed in the capturing end 526. The encoder shaft 474 may further include a second terminal end or screw engaging end 530. The screw engaging end 530 may engage the screw 424 such as with the coupling assembly 478, as discussed above. Thus, the encoder shaft 474 may be fixed to the screw 424 in a substantially axial or linear manner. However, the encoder shaft 474 may rotate with the screw 424 wherein the screw 424 is rotated by the motor 420, as noted above. The encoder shaft 474, therefore, may be an input to the encoder 502.

The encoder assembly 470 may further include a housing 534 that includes an external surface 536 and an internal surface 538. The internal surface 538 may have the shaft 474 pass therethrough. Further, one or more bearings, such as a first bearing 540 and a second bearing 544 may engage the shaft 474 to bear between the shaft 474 and the housing 434 for smooth rotation of the shaft 474.

The encoder module 502 may be fixed to the housing 434. For example, the encoder 502 may include one or more through bores 544 through which one or more fasteners, such as fasteners 546 may pass. A cover 550 may cover at least a portion of the encoder module 502. The cover 550 may include a passage or opening 554 that allows the connector 508 to connect or extend from the module 502 to the controller 32. The cover 550 may be fixed to the housing 534 with the fasteners 546 that pass through the cover 550 and/or the module 502.

The position determining assembly 470 may further include a closing or holding portion, such as an external or holding nut 560 that may engage an external thread or portion 564 that extends from the housing 534 to hold the shaft 474 in place. The housing 534 may include or define the region have the external threads 564 that extend from a first end or wall of the housing 534. A lock washer or system 568 may assist in maintaining the nut 560 on the external threads 564 relative to the housing 534. It is understood, however, that other locking or fixation holding portions may also be provided between the nut 560 and the housing 534 and/or the threaded region 564. A holding or clip member 570 may be used to hold or fix the shaft 474 in position during assembly and/or maintenance of the position determining assembly 470.

Accordingly, the position determining assembly 470 may be assembled with the encoder module 502 to assist in determining a position of various portions of the filter assembly 200. For example, the encoder shaft 474 may be fixed to the screw 424 to determine a rotational position and/or number of rotations of the screw 424. The position of the screw 424 may be used to determine a position of the frame 260 based upon the determined absolute position and/or number of turns of the screw 424 from a previous time.

Figure 8:
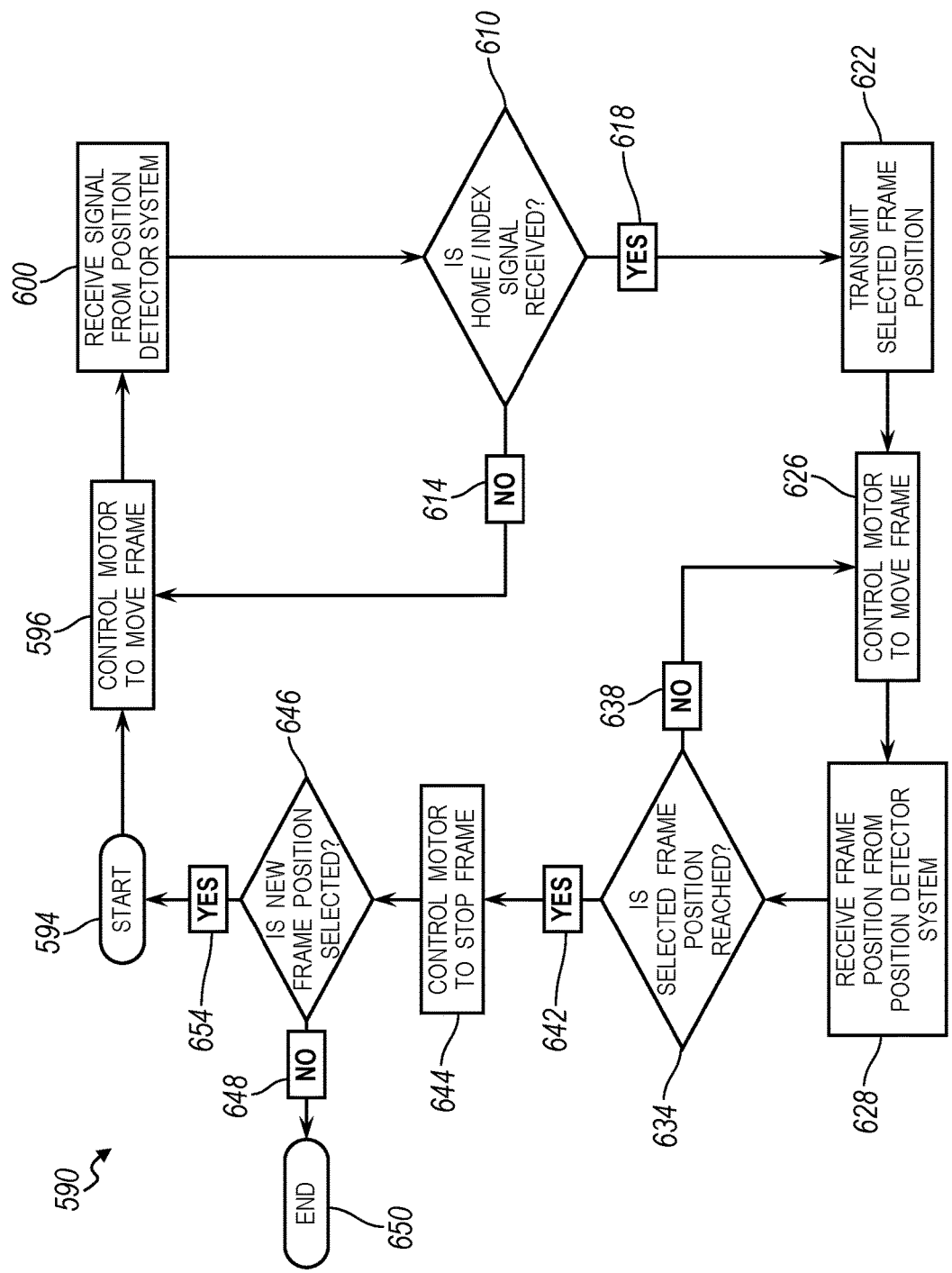
FIG. 8 is a flowchart of a process for determining a position of a filter.

Accordingly, the position sensing assembly 470, including the encoder 502, may be used to transmit a signal to the controller 32, or any appropriate controller. With continuing reference to FIG. 5 and additional reference to FIG. 8, a process 590 is illustrated. The process 590 may be controlled by the processor controller 32, or any appropriate processor system, such as those discussed herein.

Generally the process 590 may be used to move the frame 260 and/or selected filter portion thereof relative to the aperture 226. The process begins in start block 594 and a signal and/or controlling the motor to move the frame is made in block 596. As discussed above, the image controller 32 may operate the filter assembly 200, and therefore may control the motor 420. In various embodiments, however, the controller 32 may transmit a position and the motor 420 may control or include a control portion therein. Further, as also noted above, alternative and/or additional control or processor systems may be used to control the filter assembly 200. Nevertheless the motor, such as the motor 420, may be controlled to move the frame 260.

After movement of the frame and/or during movement of the frame, a signal may be transmitted and/or received from the position determining system in block 600. The position determining system may include the system 470, as noted above. The position determining system, such as including the encoder module 502, may transmit a signal during movement of the encoder shaft 474, or at other selected times. The position received or the signal sent may be an appropriate signal such as an index/home signal and/or a movement or position signal.

In various embodiments, a home or index signal may be transmitted and a determination in block 610 may be made whether the index or home signal has been sent or received. For example, the controller 32 may receive the signal through the communication line 508 (e.g. wired, wireless, or a combination thereof) and a determination may be made whether the index or home signal has been received. If the index signal has not been received, a NO-path 614 may be followed to continue movement of the frame by controlling the motor.

If an index signal has been received in block 610, a YES-path 618 may be followed based upon the receiving of the index signal. In various embodiments, a selected position of the frame 260 may be based upon the selected or determined home position. For example, the filter assembly 200 may be manufactured and/or assembled and calibrated such that the frame 260 may be moved or positioned at a home or index position. The position determining assembly 470 may determine or monitor the home position and allow for determination of movement or position of the frame 260 relative to the home position. The home position may be used to reference movement of the frame 260.

Accordingly, once the frame 260 has been determined to be in a home position in block 610 and the YES-path 618, is followed a transmission of a selected position of the frame may be made in block 622. For example, the frame 260 may be selected to be moved such that the slide or through slide filter 290 is positioned over or at the aperture 226. Accordingly, the transmission of the selected frame position may be positioning or determining an amount of movement of the frame 260 to position the slid or filter relative to the aperture 226.

Once the transmission of a selected frame position is made, the motor may be controlled through the frame in block 626. After movement and/or during movement of the frame the position of the frame from the position determining system may be received in block 628. As discussed above, the position of the frame may be determined with the position determining system 470 and/or transmitted to the controller 32. Regardless, the position of the frame may be determined and a signal may be transmitted regarding a position of the frame from the position determining system 470. The position may be a number of turns of the encoder shaft 474, time of turning of the shaft 474, absolute position of the frame 260 based on turns of the encoder shaft 474, or other appropriate position determining signal.

The controller 32 may then determine whether the frame position has reached the selected position in block 634. If a determination is made that the frame has not reached the selected position, a NO-path 638 may be followed to continue to control a motor to move the frame. Controlling movement of the frame may lead to additional receiving of a position in block 628 and a further determination of whether the frame has reached a selected position in block 634 may be made.

Once the frame has reached the selected position as determined in block 634, a YES-path 642 may be followed to control the motor to stop the frame in block 644. Once the frame is stopped due to controlling the motor in block 644 appropriate operations may occur. For example, images may be collected with the imaging system 10 to generate projections of the subject 14. It is understood that other appropriate operations may occur after stopping the frame in block 644, as one skilled in the art will understand.

After stopping the frame in block 644, a determination may be made of whether a new position is selected in block 646. For example, a procedure may continue to acquire further projections of the subject 14, a different subject, or other appropriate portions. If no new positions are selected, a NO-path 648 may be followed and the process may end at block 650. Ending the process in block 650 may include any appropriate procedure, such as performing a procedure on a subject 14, moving the imaging system 10, or other appropriate steps.

However, if a new position is selected in block 646, a YES-path 654 may be followed to restart in block 594. Accordingly, the frame may be moved to the home or index position, as discussed above, and a new position for the frame may be selected and the frame may be moved as noted above. It is understood that the frame need not be moved to the index position of a time after initiating the frame to a home or index position, however, it may be selected to do so. By moving the frame to the index position prior to moving the frame to any other selected position, the position of the frame may always be moved relative to the single home or index position to assist in achieving a precise placement of the frame 260 relative to the aperture 226.

Figure 9:
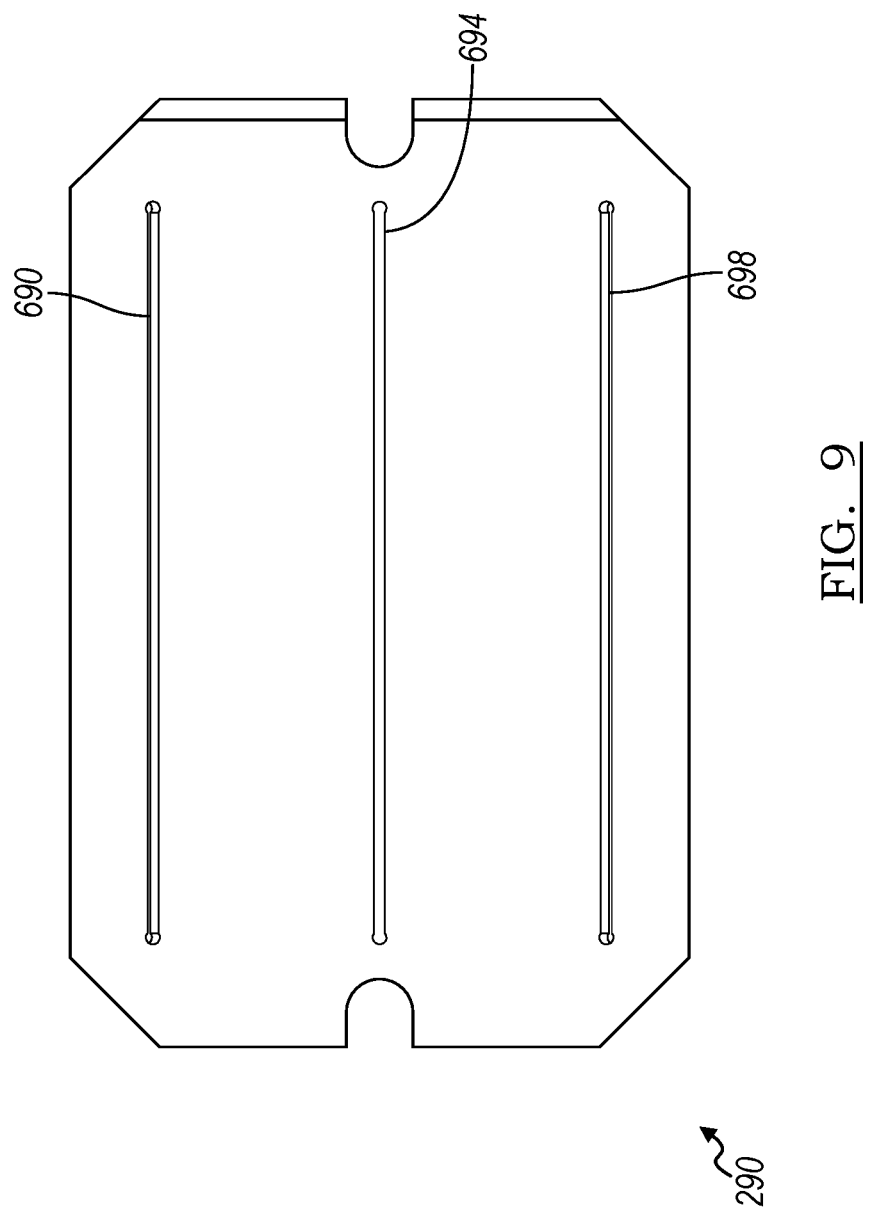
FIG. 9 is a detailed view of a slotted filter.

In various embodiments, as noted above, the frame assembly 200 may include the slotted filter member 290 as illustrated in FIG. 9. The slotted filter member 290 may include the filter member disclosed in U.S. Pub. No. 2020-0205763, incorporated herein by reference. The slotted filter 290 may include a plurality of slots, such as a first slot 690, a second slot 694, and a third slot 698. The slots 690-698 may be formed in the filter member 290 to extend through the filter member 290 from a first side to a second side. Further the slots may be spaced apart across the filter 290 at a selected position. In various embodiments, the outside slots 690, 698 may be angled relative to a central axis or relative to a normal axis of a surface of the filter member 290. The central slot 694 may extend along an axis that substantially normal to the surface of the filter member 290. The filter member 290 may be formed of a material that substantially blocks or eliminates transmission of x-rays from the source 100. Accordingly, positioning the slotted filter member 290 over the aperture 226 may cause x-rays to pass through only the slot 690-698 to reach the subject 14 and the detector 38.

In various embodiments, the positioning the slotted filter 290 relative to the source 100 and/or the detector 38 may be selected to be substantially precise and repeatable. For example, it may be selected to position the slotted filter 290 relative to the aperture 226 in a repeatable manner and/or substantially precise manner that is repeatable with a variance that is less than about 0.00025 in (about 0.0064 mm) to about 0.003 in (about 0.08 mm), including about 0.00075 in (about 0.019 mm). In various embodiments, the repeatability and/or absolute position of the slotted filter 290 may be selected to be substantially within 10% of an absolute selected position. Accordingly, the x-ray assembly 422 in combination with the position determination system 470 may be used to substantially achieve and/or achieve the substantial precise positioning of the slot filter 290 relative to the aperture 226. In various embodiments, a speed or rate of movement of the system (e.g. the filter 290) moves may be a function of the motor torque/speed curve in conjunction with the leadscrew selected. In various embodiments, the speed may be about 0.4 in/sec (about 10 mm/sec). It is understood, however, that other appropriate speeds may also be achieved with an appropriate motor and screw pitch sized accordingly.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.1 lad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system to position a filter in an imaging system, comprising:
   a mounting plate defining an aperture through the mounting plate;
   a filter frame having at least a first filter holding portion operable to move relative to the aperture;
   a movement system configured to move the filter frame relative to the aperture, the movement system having:
   a motor;
   a rail extending between a first end and a second end and movably attached to the filter frame, wherein the rail extends along a first side of the filter frame;
   a rotatable shaft configured to be rotated by the motor, wherein the shaft extends along a second side of the filter frame opposed to the first side;
   a connection member connected to the shaft and the filter frame, wherein the connection member is operable to move relative to the rail when the shaft is rotated by the motor; and
   a position determining assembly having a sensor operable to sense a rotation of the shaft.

2. The system of claim 1, wherein the position determining assembly comprises:
   a position determination module connected to the sensor;
   a communications link;
   an input portion operable to be sensed by the sensor;
   wherein the input portion is axially fixed to the shaft.

3. The system of claim 1, further comprising:
   a filter member carried by the filter frame at the first filter holding portion;
   wherein the filter member includes a plurality of slots extending therethrough operable to be precisely positioned relative to the aperture.

4. The system of claim 1, further comprising:
   a bushing having a first engaging surface and a second engaging surface;
   wherein the first engaging surface extends at an angle relative to the second engaging surface;
   wherein the first engaging surface engages a first surface of the frame and the second engaging surface engages a second surface of the frame.

5. The system of claim 1, further comprising:
   a processor;
   wherein a position determination module is operable to generate an index pulse when the filter frame is at a home position;
   wherein the index pulse is transmitted as an index signal to the processor;
   wherein the processor is operable to determine that at least a first filter holding portion is at a home position based on the index signal.

6. The systems of claim 1, wherein the shaft includes an extension thread.

7. A system to position a filter in an imaging system, comprising:
   a mounting plate defining an aperture through the mounting plate;
   a rail extending between a first end and a second end and fixed to the mounting plate;
   a motor;
   a screw configured to be rotated by the motor, wherein the screw includes an exterior thread;
   a filter frame having at least a first filter holding portion; and
   a position determining module;
   wherein the position determining module is operable to sense a rotation of the screw;
   wherein the rail extends along a first side of the filter frame and the screw extends along an opposite second side of the filter frame.

8. The system of claim 7, further comprising:
   a position determination system comprising at least the position determining module and an input portion;
   wherein the input portion is fixed to the screw.

9. The system of claim 7, further comprising:
   a connection member having internal threads to engage the external threads of the screw, wherein the connection member is operable to move relative to the rail when the screw is rotated by the motor;
   wherein the filter frame is moveably connected to the screw through the connection member and the rail.

10. The system of claim 7, wherein the screw rotates relative to the rail, but is linearly fixed relative to the rail.

11. The system of claim 7, further comprising:
    a bushing having a first engaging surface and a second engaging surface;
    wherein the first engaging surface extends at an angle relative to the second engaging surface;
    wherein the first engaging surface engages a first surface of the frame and the second engaging surface engages a second surface of the frame.

12. The system of claim 7, wherein the positioning determining module is spaced away from the motor and fixedly connected to the screw.

13. The system of claim 7, further comprising:

a filter member having at least a first through slot, a second through slot, and a third through slot;

wherein the first through slot, the second through slot, and the third through slot are spaced apart and configured to be positioned over the aperture with the rotation of the screw.

14. The system of claim 7, further comprising:

a processor;

wherein the position determining module is operable to generate an index pulse when the frame is at a home position;

wherein the index pulse is transmitted as an index signal to the processor;

wherein the processor is operable to determine that at least a first filter holding portion is at a home position based on the index signal;

wherein the processor is further operable to receive a position signal from the position determining module;

wherein the processor is operable to execute instructions to determine a position of the at least a first filter holding portion relative to the aperture.

15. A method of positioning a filter in an imaging system, comprising:

operating a motor system to rotate a shaft;

moving a frame member coupled to the shaft with the motor system;

sensing a position of the frame member based on rotation of the shaft and transmitting at least one of (i) an index position of a frame member or (ii) a position of the shaft; and sending a signal from a position sensing system to a processor regarding the sensed position of the frame member;

wherein the position sensing system is separate from the motor system.

16. The method of claim 15, further comprising:

operating a control system to select a filter to filter an imaging beam;

transmitting a selected filter position;

wherein operating the motor system to rotate the shaft includes rotating the shaft to move the frame member to a selected position.

17. The method of claim 15, further comprising:

moving the frame member by operating the motor system to rotate the screw until the index position is transmitted.

18. The method of claim 15, further comprising:

receiving the signal at the control system;

determining the real time position of the frame member;

sending a stop signal when the real time position of the frame member matches within a threshold the selected filter position.

19. The method of claim 15, further comprising:

movably fixing the frame member to a rail member.

20. The method of claim 15, further comprising:

connecting the position sensing system to the shaft.

* * * * *

UNITED STATES PATENT AND TRADEMARK OFFICE
CERTIFICATE OF CORRECTION

PATENT NO. : 11,678,849 B2
APPLICATION NO. : 17/321741
DATED : June 20, 2023
INVENTOR(S) : David A. Garlow et al.

It is certified that error appears in the above-identified patent and that said Letters Patent is hereby corrected as shown below:

In the Specification

Column 6, Detailed Description, Line 59, Delete "150" and insert --200-- therefor Column 9, Detailed Description, Line 10, Delete "26," and insert --22,-- therefor Column 12, Detailed Description, Line 12, Delete "busing" and insert --bushing-- therefor Column 13, Detailed Description, Line 41, Delete "424" and insert --420-- therefor Column 16, Detailed Description, Line 6, Delete "fo" and insert --of-- therefor Column 16, Detailed Description, Line 13, Delete "420" and insert --470-- therefor Column 21, Detailed Description, Line 15, Delete "802.1 lad," and insert --802.11ad,-- therefor In the Claims Column 22, Claim 9, Line 48, delete "comprising;" and insert --comprising:-- therefor Signed and Sealed this
Tenth Day of October, 2023

Katherine Kelly Vidal
*Director of the United States Patent and Trademark Office*